United States Patent [19]
Kato et al.

[11] Patent Number: 5,912,334
[45] Date of Patent: Jun. 15, 1999

[54] DNA ENCODING EQUINE INTERLEUKIN-1

[75] Inventors: Hirotomo Kato; Noriko Nakamura; Hiroko Aida; Shigeyoshi Takagi, all of Tokyo; Toshihiro Watari, Kanagawa; Hajime Tsujimoto; Atsuhiko Hasegawa, both of Tokyo, all of Japan

[73] Assignee: Hitachi Chemical Company, Ltd., Tokyo, Japan

[21] Appl. No.: 08/611,880

[22] Filed: Mar. 6, 1996

[30] Foreign Application Priority Data

Sep. 4, 1995 [JP] Japan .................................. 7-226133

[51] Int. Cl.$^6$ ........................... C12N 15/25; C12N 15/63; C07K 14/545
[52] U.S. Cl. ................ 536/23.5; 435/71.2; 435/325; 435/252.3; 435/320.1; 435/471; 530/351
[58] Field of Search .................. 536/23.1, 23.5; 435/71.1, 71.2, 172.3, 325, 252.3, 320.1, 471; 935/11, 22, 66, 72, 73; 530/351

[56] References Cited

U.S. PATENT DOCUMENTS 4,766,069 8/1988 Auron et al. ............................. 435/70
4,894,333 1/1990 Cerretti et al. ......................... 435/69.52

OTHER PUBLICATIONS

Nishida et al. (1987) Biochem. Biophys. Res. Comm. vol. 143, No. 1, pp. 345–352.

Harlow et al. (1988) Antibodies & Laboratory Manual, Ch. 5. p. 76, Cold Spring Harbor Laboratory.

Mori et al. (1988) Biochem. Biophy. Res. Comm. vol. 150 pp. 1237–1243.

Furutaui et al. (1985) Nucl. Acids Res. vol. 13, No. 16, pp. 5869–5882.

March et al. (1985) Nature vol. 315, No. 6021, pp. 641–647.

Cannon et al. (1989). J. of Immunol. vol. 142, No. 7, pp. 2299–2306.

Leong et al. (1988) Nucl. Acids Res. vol. 16, No. 18, p. 9053.

Maliszewski et al. (1990) Nucl. Acids Res. vol. 18, No. 14, p. 4782.

*Primary Examiner*—Prema Mertz
*Attorney, Agent, or Firm*—Antonelli, Terry, Stout & Kraus, LLP

[57] ABSTRACT

Disclosed are a equine interleukin-1 peptide which comprises a sequence comprising at least 5 continuous amino acids in a peptide represented by SEQ ID NO: 1 or NO: 2 in the sequence listing, DNA coding the equine interleukin-1 peptide, a recombinant vector containing the DNA, a transformant containing the recombinant vector, and a process for preparing an anti-equine interleukin-1 antibody, which comprises using the equine interleukin-1 peptide as an antigen.

15 Claims, No Drawings

DNA ENCODING EQUINE INTERLEUKIN-1

BACKGROUND OF THE INVENTION

1. Field of the Invention

This invention relates to an equine interleukin-1 peptide, DNA coding the same, a recombinant vector containing the DNA, a transformant containing the recombinant vector, and a process for preparing an anti-equine interleukin-1 antibody.

2. Prior Art

With respect to a horse, inflammatory diseases such as pneumonia, arthritis and laminitis have been clinically serious problems, and basic researches on measurement of cytokines and cytokine treatment have been important tasks.

On the other hard, an inflammatory cytokine has been known as a factor of endogenous fever and a factor of destroying chondrocytes. Interleukin-1 is the above inflammatory cytokine and participates in activation of cells. Two types, i.e., α type and β type of interleukin-1 have been known.

The structure of interleukin-1 of a human, a mouse or the like has heretofore been determined (P. T. Lomedico et al., "Nature", Vol. 312, P. 458 (1984) and C. J. March et al., "Nature", Vol. 315, p. 641 (1985)). However, the structure of equine interleukin-1 has not yet been determined. This fact is an obstacle in researching relations between equine interleukin-1 and the above inflammatory diseases and also a bottleneck in developing medicines for diagnosing inflammatory diseases from relations with equine interleukin-1.

SUMMARY OF THE INVENTION

The invention provides an equine interleukin-1 peptide represented by SEQ ID NO: 1 or NO: 2 which is important for researching relations between equine inflammatory diseases and equine interleukin-1.

The invention provides the effect of the invention described herein and also an α type equine interleukin-1 peptide represented by SEQ ID NO: 1 which is important for researching relations between equine inflammatory diseases and a subtype (α type) of equine interleukin-1.

The invention provides, in addition to the effect of the invention described herein a β type equine interleukin-1 peptide represented by SEQ ID NO: 2 which is important for researching relations between equine inflammatory diseases and a subtype (β type) of equine interleukin-1.

The invention provides DNA coding the equine interleukin-1 peptide or DNA complementary thereto, which is important for researching relations between equine inflammatory diseases and equine interleukin-1.

The invention provides, in addition to the effect of the invention described herein a DNA coding the α type equine interleukin-1 peptide represented by SEQ ID NO: 3, which is important for researching relations between equine inflammatory diseases and a subtype (α type) of equine interleukin-1.

The invention provides, in addition to the effect of the invention described herein a DNA coding the β type equine interleukin-1 peptide represented by SEQ ID NO: 4, which is important for researching relations between equine inflammatory diseases and a subtype (β type) of equine interleukin-1.

The invention provides a recombinant vector containing the DNA coding the equine interleukin-1 peptide or DNA complementary thereto, which is important for researching relations between equine inflammatory diseases and equine interleukin-1.

The invention provides, in addition to the effect of the invention described herein a recombinant vector plasmid pCEα containing the DNA coding the α type equine interleukin-1 peptide, which is important for researching relations between equine inflammatory diseases and a subtype (α type) of equine interleukin-1.

The invention provides, in addition to the effect of the invention described herein, to provide a recombinant vector plasmid pEβ5, containing the DNA coding the α type equine interleukin-1 peptide, which is important for researching relations between equine inflammatory diseases and a subtype (β type) of equine interleukin-1.

The invention provides a transformant containing the DNA coding the equine interleukin-1 peptide or DNA complementary thereto, which is important for researching relations between equine inflammatory diseases and equine interleukin-1.

The invention provides, in addition to the effect of the invention described herein a transformant containing the DNA coding the α type equine interleukin-1 peptide deposited as FERM P-15142 in NATIONAL INSTITUTE OF BIOSCIENCE AND HUMAN TECHNOLOGY (NIBH) at 1–3, Higashi 1-chome, Tsukuba-shi, IBARAKI-KEN 305 JAPAN, which is important for researching relations between equine inflammatory Diseases and a subtype (α type) of equine interleukin-1.

The invention provides, in addition to the effect of the invention described herein a transformant containing the DNA coding the β type equine interleukin-1 peptide deposited as FERM P-15143 in NIBH, which is important for researching relations between equine inflammatory diseases and a subtype (β type) of equine interleukin-1.

The invention provides a process for preparing an anti-equine interleukin-1 antibody, which is important for researching relations between equine inflammatory diseases and equine interleukin-1.

The present invention relates to the following (1) to (13).

(1) An equine interleukin-1 peptide which comprises a sequence comprising at least 5 continuous amino acids in a peptide represented by SEQ ID NO: 1 or NO: 2 in the sequence listing shown below.

(2) The peptide described in the above (1), wherein said peptide is a peptide represented by SEQ ID NO: 1.

(3) The peptide described in the above (1), wherein said peptide is a peptide represented by SEQ ID NO: 2.

(4) DNA which comprises coding the peptide described in any of the above (1) to (3), or DNA complementary thereto.

(5) The DNA described in the above (4), wherein said DNA has a base sequence of SEQ ID NO: 3 in the sequence listing shown below.

(6) The DNA Described in the above (4), wherein said DNA has a base sequence of SEQ ID NO: 4 in the sequence listing shown below.

(7) A recombinant vector which comprises the DNA described in any of the above (4) to (6).

(8) The recombinant vector described in the above (7), wherein said vector is plasmid pCEα.

(9) The recombinant vector described in the above (7), wherein said vector is plasmid pEβ5.

(10) A transformant which comprises the recombinant vector described in any of the above (7) to (9).

(11) The transformant described in the above (10), wherein aid transformant is deposited as FERM P-15142.

(12) The transformant described in the above (10), wherein said transformant is deposited as FERM P-15143.

(13) A process for preparing an anti-equine interleukin-1 antibody, which comprises using the peptide described in any of the above (1) to (3) as an antigen.

DESCRIPTION OF THE PREFERRED EMBODIMENTS

In the following, the present invention is explained in detail.

Equine interleukin-1

As described above, interleukin-1 is an inflammatory cytokine and participates in activation of cells, and there are two types, i.e., α type and β type of interleukin-1.

α type equine interleukin-1 is a peptide represented by SEQ ID NO: 1, and β type equine interleukin-1 is a peptide represented by SEQ ID NO: 2. In the sequence listing, the amino acid sequences are each started from an amino acid at the end of an amino group (hereinafter the same).

Equine interleukin-1 peptide

The equine interleukin-1 peptide in the present invention is a generic name which includes the above equine interleukin-1, a part thereof and a peptide containing the equine interleukin-1 or a part thereof.

The above equine interleukin-1 peptide is required to have antigenicity as; equine interleukin-1.

From the point of the minimum size by which equine interleukin-1 has antigenicity, the equine interleukin-1 peptide is preferably a peptide having a sequence comprising at least 5 continuous amino acids in the peptide represented by SEQ ID NO: 1 or NO: 2 (hereinafter referred to as "Peptide A").

As Peptide A, there may be mentioned, for example, the peptide represented by SEQ ID NO: 1, and said peptide has the entire amino acid sequence of a type equine interleukin-1.

As Peptide A, there may be also mentioned the peptide represented by SEQ ID NO: 2, and said peptide has the entire amino acid sequence of β type equine interleukin-1.

These peptides have antigenicities as equine interleukin-1.

When the amino acid sequence derived from equine interleukin-1 contained in the peptide chain of the equine interleukin-1 peptide is long, an antigen-antibody reaction with high sensitivity can be expected, and also high biological activities (power of destroying chondrocytes or the like) can be expected. Therefore, Peptide A is preferably a peptide having a sequence comprising 20 or more continuous amino acids, more preferably a peptide having a sequence comprising 200 or more continuous amino acids in the peptide represented by SEQ ID NO: 1. As such a peptide, there may be mentioned, for example, the peptide represented by SEQ ID NO: 1 and the peptide represented by SEQ ID NO: 2 described above.

From the point of heightening antigenicity, Peptide A is preferably a peptide having a sequence in which a sequence comprising at least 5 continuous amino acids in the peptide represented by SEQ ID NO: 1 is repeated. As the sequence which is a recurring unit, there may be mentioned, for example, the amino acid sequence of the peptide represented by SEQ ID NO: 1 and the amino acid sequence of the peptide represented by SEQ ID NO: 2. The recurring number of times is not particularly limited, but it is generally once to 10 times.

The recurring units are bonded to each other directly or through an intervenient sequence. As the intervenient sequence, there may be mentioned, for example, an amino acid sequence. The number of amino acids contained in the above amino acid sequence is not particularly limited, but it is generally 1 to 50. As a specific examples of the above amino acid sequence, there may be mentioned, for example, an amino acid sequence comprising alanine-alanine-alanine.

So long as antigenicity as equine interleukin-1 is maintained, Peptide, A may be a peptide represented by SEQ ID NO: 1 or NO: 2 from which some of amino acids (e.g., 1 to 263 amino acids) are lacking. If the number of amino acids lacking are too large, antigenicity as equine interleukin-1 of Peptide A tends to be impaired.

When the number of amino acids lacking is large (e.g., 5 or more), antigenicity as equine interleukin-1 is easily lowered. Therefore, in order to minimize such lowering, it is preferred that the amino acids lacking from the peptide represented by SEQ ID NO: 1 or NO: 2 are continuous.

Further, so long as antigenicity as equine interleukin-1 is maintained, a peptide having an amino acid sequence derived from equine interleukin-1 and also other amino acid sequence can he used as Peptide A, but it is required that such a peptide has no antigenicity or lower antigenicity as a compound other than equine interleukin-1 relative to antigenicity as equine interleukin-1.

As an example of the above peptide, there may be mentioned a peptide represented by SEQ ID NO: 1 or NO: 2 in which an amino acid(s) is/are replaced with other amino acid(s), a peptide represented by SEQ ID NO: 1 or NO: 2 in which an amino acid(s) is/are inserted, and a peptide represented by SEQ ID NO: 1 or NO: 2 in which an amino acid(s) or other peptide is/are bonded to a sequence comprising at least 5 continuous amino acids directly or through an intervenient sequence.

When the number of amino acids to be replaced or inserted is large (e.g., 5 or more) or when the number of amino acids contained in other peptide to be bonded is large (e.g., 1,000 or more), antigenicity as equine interleukin-1 is easily lowered. Therefore, in order to minimize such lowering, it is preferred that the amino acids to be replaced with or inserted in the peptide represented by SEQ ID NO: 1 or NO: 2 are continuous, and it is also preferred that the other peptide to be bonded has a sequence comprising less than 1,000 amino acids.

It is preferred that the amino acid(s) to be replaced has/have similar characteristics, and there may be mentioned, for example, replacement of glycine with alanine.

As the amino acid(s) or other peptide to be bonded, there may be mentioned, for example, alanine, alanine-alanine-alanine and β-galactosidase.

As the intervenient sequence, there may be mentioned those described above.

The above intervenient sequence, an amino acid(s) or other peptide may be bonded either of an amino group end side or a carboxyl group end side of the sequence comprising at least 5 continuous amino acids in the peptide represented by SEQ ID NO: 1 or NO: 2.

Process for preparing equine interleukin-1 peptide

As a process for preparing the equine interleukin-1 peptide in the present invention, there may be mentioned, for example, a chemical synthetic method and a genetic recombination method.

As the chemical synthetic method, there may be mentioned, for examples MAP (Multiple Antigen Peptide) method. The MAP method is suitable for synthesizing a peptide having a sequence comprising 30 or less amino acids, and synthesis can be carried out by using a commercially available peptide-synthesizing machine. A peptide can be synthesized in the form of repetition by the MAP method.

As the genetic, recombination method, there may be mentioned, for example, a method in which DNA coding the equine interleukin-1 peptide of the present invention is inserted into a vector to form a recombinant vector, the recombinant vector is inserted into a host to prepare a transformant, and the desired peptide is purified from the transformant.

The DNA coding the equine interleukin-1 peptide of the present invention is described below.

As the vector, there may be mentioned, for example, a plasmid and a phage.

As the host, there may be mentioned, for example, *Escherichia coli, Bacillus subtilis* and yeast.

In the following, a process for preparing a transformant and a process for purifying the desired peptide by using the transformant are described in detail.

The recombinant vector containing the DNA of the present invention can be prepared by inserting the DNA (described below) coding the equine interleukin-1 peptide into an existing plasmid vector, phage vector or the like according to the conventional method. In that case, if necessary, a linker is used. When the inserted DNA is expressed, it is required that the position into which the DNA is to be inserted is downstream in a promoter region. As the existing plasmid vector, there may be mentioned, for example, pBR322, pUC18, pUC19 and pCR2 (trade names, all produced by Invitrogen Co., U.S.A.) and Bluescript SK(−) (trade name, produced by Stratagene Co., U.S.A.), and as the phage vector, there may be mentioned, for example, λgt10 and λgt11. These Erectors are all commercially available, and recombinant vectors corresponding to used parent vectors can be obtained.

As the recombinant vector containing the DNA of the present invention, there may be mentioned pCEα and pEβ5 as described belong.

The obtained recombinant vector is inserted into a host to prepare a transformant. When a plasmid or γ phage derived from *Escherichia coli* is used, *Escherichia coli*, for example, an *Escherichia coli* HB101 strain can be used as the host. The host is generally treated so as to be competent cells. The competent cells obtained by treating the *Escherichia coli* HB101 strain are available from Takara Shuzo Co., Japian. As a process for preparing the transformant by using *Escherichia coli*, there may be used, for example, a process in which *Escherichia coli* at the first half of a logarithmic growth period is washed with an about 20 mM calcium chloride solution under ice cooling, *Escherichia coli* is suspended in the above calcium chloride solution, a recombinant vector is added to the suspension, and the mixture is incubated at 42° C. for 1 to 2 minutes.

The recombinant vector and the transformant can be also prepared by using a commercially available kit. As such a kit, there may be mentioned TA-Cloning Kit (trade name) produced by In-vitrogen Co. in U.S.A. and Qiagen Plasmid Kit (trade name) produced by Qiagen Co. in U.S.A.

A common means for obtaining a transformant by using a recombinant vector is described in J. Samblook et al., "Molecular Cloning" 2nd ed., Cold Spring Harbor Laboratory Press (1989), his literature is hereinafter referred to as "the literature "Molecular Cloning"").

As a process for culturing the transformant, there may be used, for example, a process in which an incubator is shaken at suitable temperature until the equine interleukin-1 peptide is sufficiently accumulated in the transformant in a medium in which the transformant can be grown. As the medium, there may be used, for example, a LB medium, a TB medium and a 2×TY medium. The culture temperature is, for example, 35 to 42° C. when *Escherichia coli* is used as the host. When the recombinant vector can express antibiotic-resistant genes, it is preferred from the point of suppressing growth of a transformant having no recombinant vector that the antibiotic is added to the medium. As such an antibiotic, there may be mentioned, for example, ampicillin. The culture time varies depending on the kind of the host, an incubation apparatus, the culture temperature and the concentration of the transformant in a culture solution when culture is started, but when culture is carried out under shaking at 37° C. by using a LB medium, the culture time is generally one night. Common means of a preparation process of a LB medium, TB medium or 2×TY medium and a culture process are described in the literature "Molecular Cloning".

As a method of pulverizing the cultured transformant, there may be used, for example, a method in which the transformant is collected by centrifugation and then suspended in a buffer solution to prepare a suspension, and physical impact is given to the suspension. As the buffer solution, there may be used, for example, a TE buffer solution. As a method of giving physical impact to the above suspension, there may be used, for example, a method of irradiating ultrasonic waves on the above suspension.

When the transformant is *Escherichia coli*, there may be also used, for example, a method in which the transformant is dissolved by adding lysozyme to the above suspension, adding a TE buffer solution containing sodium dodecylsulfate (SDS) thereto and stirring the mixture, in place of giving physical impact to the above suspension.

After the transformant is pulverized or dissolved, the cellular residue is removed by centrifugation to obtain a supernatant.

When the desired peptide is a fused protein in which a signal peptide is bonded to an amino end side thereof (i.e., the desired peptide can be secreted extracellularly), there may be used a method in which the culture solution is centrifuged to obtain a supernatant.

As a process for purifying the peptide, there may be mentioned, for example, the respective steps of removing nucleic acid by adding streptomycin sulfate and obtaining a protein by adding ammonium sulfate.

As the step of removing nucleic acid by adding streptomycin sulfate, there may be used, for example, an operation in which streptomycin sulfate is added to either of the above supernatants, and the mixture is stirred for a while and then centrifuged to remove nucleic acid as precipitates and obtain a supernatant.

As the step of obtaining a protein by adding ammonium sulfate, there may be used, for example, an operation in which ammonium sulfate is added to the supernatant after removing nucleic acid as precipitates, the mixture is stirred and then centrifuged. In general, precipitates are obtained, but the desired peptide may be contained in the supernatant so that it is preferred to confirm presence or absence of the desired peptide by sampling.

Subsequently, a step of obtaining a fraction containing the equine interleukin-1 peptide is carried out. As this step, there may be used, for example, a method in which a solution obtained by dissolving the above precipitates in a small amount of a buffer solution or the above supernatant is fractionated by liquid chromatography to identify a fraction containing the equine interleukin-1 peptide. In order to identify the fraction containing the equine interleukin-1 peptide, there may be used, for example, electrophoresis using a molecular weight as an index, and a bioassay using a biological activity such as power of destroying chondrocyte(s as an index. The molecular weight of the equine interleukin-1 peptide can be determined from an amino acid sequence thereof. Specific methods of removing residues such as cell membrane, removing nucleic acid by adding streptomycin sulfate and obtaining a protein by adding ammonium sulfate are described in the literature "Molecular Cloning".

When the vector contained in the transformant is a vector which can produce the peptide coded by the inserted DNA as a fused protein with other peptide, the equine interleukin-1 peptide can be purified by using characteristics of this "other peptide".

DNA coding the equine interleukin-1 peptide

In the present invention, the DNA coding the equine interleukin-1 peptide is DNA coding Peptide A. This DNA is DNA selected from the group of DNAs when the amino acids of the amino acid sequence of Peptide A are converted into a base sequence according to the triplet code table.

In the present invention, the DNA coding the peptide represented by SEQ ID NO: 1 or NO: 2 is DNA selected from the group of DNAs (including DNAs having base sequences represented by SEQ ID NO: 3 and NO: 4, respectively) when the amino acids of the peptide represented by SEQ ID NO: 1 or NO: 2 are converted into a nucleotide sequence according to the triplet cocie table (1 to 6 nucleotide sequences are allotted to th(e respective amino acids).

As Peptide A, there may be mentioned the peptides in the above description about the equine interleukin-1 peptide, and as the DNA coding Peptide A, there may be mentioned DNAs having nucleotide sequences corresponding to the amino acid sequences of these peptides.

In the sequence listing, the base sequences are each started from a base at 5'-end (hereinafter the same).

The DNA coding Peptide A can be prepared by a chemical synthetic method or a genetic recombination method.

As the chemical synthetic method, there may be mentioned, for example, a phosphoamidide method. The phosphoamidide method is suitable for synthesizing DNA having a base sequence with a total length of 100 or less bases, and chemical synthesis can be carried out by using a commercially available DNA-synthesizing machine.

In order to prepare DNA having a base sequence with a total length which is longer than 100 bases, a genetic recombination method described below can be used, but such DNA can be also prepared in the following manner.

That is, the ease sequence is divided into less than 100 bases, chemically synthesizing DNA fragments comprising the respective base sequences as described above, mixing the DNA fragments and linking the DNA fragments by using T4-DNA ligase. In that case, when protruding ends are made to be produced after synthesizing DNA fragments of complementary strands and at the time of facing the DNA fragments to each other, the protruding ends fulfill a role of adhesive ends, whereby the desired DNA can be obtained easily.

As the genetic recombination method, there may be mentioned, for example, a method in which complementary DNA (cDNA) is prepared by using peripheral blood mononuclear cells (PBMC) of a horse, and the cDNA coding the equine interleukin-1 peptide is amplified by using a primer prepared based on a base sequence stored in interleukin-1 genes of other organism, as described below. By the genetic recombination method, long DNA comprising 100 or more bases can be prepared.

The base sequence of the DNA can be determined according to the conventional method. As a method of determining the base sequence, there may be mentioned, for example, a dideoxy termination method, and a commercially available kit can be used. Such a kit is available from Pharmacia Co. in Sweden or the like.

Next, a process for obtaining cDNA coding the equine interleukin-1 peptide from horse PBMC is described in detail.

First, blood (peripheral blood or the like) is obtained from a horse (a thoroughbred or the like) and subjected to centrifugation or the like to obtain a PBMC fraction, and this fraction is cultured. As a culture process, there may be used, for example, a process in which the PBMC fraction is incubated a, suitable temperature (e.g., 37° C.) for 24 hours under existence of carbon dioxide (e.g., 5% (v/v)) in a medium for culturing animal cells, which contains bovine fetal serum, gentamicin and lipopolysaccharide. As the medium for culturing animal cells, there may be used, for example, a RPMI1640 medium (trade name, produced by Nissui Seiyaku Co., Japan).

Subsequently, the PBMC cells are collected by centrifugation or the like and then dissolved to obtain a cell extract. As a method of obtaining the cell extract by dissolving the cells, there may be used, for example, a method in which the cells are frozen in liquid nitrogen, the frozen cells are suspended in a dissolved buffer solution, and the suspension is incubated. As the dissolved buffer solution, there may be mentioned, for example, Trishydrochloride (10 mM, pH 7.4) containing proteinase K (20 $\mu$g/ml), ethylenediaminetetraacetic acid (EDTA, 1 mM) and sodium dodecylsilfate (SDS, 0.5%).

By using polydeoxythymidylic acid or the like, polyadenylic acid-bonded RNA (hereinafter abbreviated to "Poly (A)+RNA") is obtained from the obtained cell extract.

A common means for obtaining Poly(A)+RNA from cells is described in he literature "Molecular Cloning", but a kit available from Invitrogen Co. or the like can be also used.

According to the conventional method, cDNA is prepared from the obtained Poly(A)+RNA. A common means for preparing cDNA is described in the literature "Molecular Cloning", but a kit available from Pharmacia Co. or the like can be also used.

Next, a process for obtaining the cDNA coding the equine interleukin-1 peptide by amplification using a primer prepared based on a base sequence stored in interleukin-1 genes of other organism is described in detail.

As a method of amplifying the cDNA, there may be mentioned, for example, a method in which a primer, a polymerase (Taq polymerase or the like) and deoxyribonucleotides are added to the obtained cDNA, and steps of heating, cooling and incubating the mixture are repeated. As the primer, there may be used a DNA fragment having a base sequence commonly stored between human and mouse interleukin-1 genes (P. T. Lomedico et al., "Nature", Vol. 312, p. 458 (1984) and C. J. March et al., "Nature", Vol. 315, p. 641 (1985)) or a base sequence complementary thereto. As such DNA, there may be mentioned DNA fragments having base sequences of SEQ ID NO: 5 to ID NO: 8 in the sequence listing shown below.

The base sequence of SEQ ID NO: 5 is a base sequence located at an upstream side of the code area of the peptide among base sequences of human and mouse interleukin-1α genes, and the base sequence of SEQ ID NO: 6 is a base sequence which is complementary to a base sequence located at a downstream side of this code area. Therefore, it is estimated that the cDNA to be amplified would contain the entire code area of the equine interleukin-1α peptide.

On the other hand, the base sequences of SEQ ID NO: 7 and NO: 8 are a base sequence commonly stored in human and mouse interleukin-1β genes and a base sequence complementary thereto, respectively. However, judging from a locational relation between these base sequences, it is estimated that the cDNA to be amplified would not contain the entire code area of the equine interleukin-1β peptide, but contain a part thereof.

A common means for this DNA-amplifying method has been known as the Polymerase Chain Reaction (PCR) method, and details thereof are described in the literature "Molecular Cloning".

When the obtained cDNA does not contain the entire code area of the equine interleukin-1 peptide, genome walking or the like is further carried out, whereby the DNA containing the entire code area can be obtained. For genome walking, a commercially available kit may be used.

Once the DNA coding the equine interleukin-1 peptide is obtained, the DNA can be replicated by using the genetic recombination method or the above PCR method so that it is not necessary to carry out an operation of obtaining the DNA coding the equine interleukin-1 peptide again from horse PBMC.

A method using -he genetic recombination method is carried out, for examples, in the following manner. First, as described above, the obtained DNA coding the equine interleukin-1 peptide is inserted into an existing plasmid vector, phage vector or the like to prepare a recombinant vector, the recombinant vector is inserted into a host to prepare a transformant, and the transformant is cultured. By this culture, the recombinant vector is amplified in the transformant. The amplified recombinant vector is obtained from the transformant, and the DNA coding the equine interleukin-1 peptide is cut out by using a restriction enzyme. The operation of obtaining the amplified recombinant vector from the transformant can be carried out, for example, in the following manner. When the recombinant vector is a plasmid, a transformant thereof is pulverized and subjected to phenol/chloroform treatment and ethanol precipitation treatment to obtain DNA. By using ethidium bromide-containing cesium chloride, the obtained DNA is subjected to ultracentrifugation to obtain the recombinant vector as plasmid DNA. On the other hand, when the recombinant vector is a phage, a transformant thereof is pulverized to obtain phage particles, the phage particles are dissolved to obtain the recombinant vector as phage DNA.

As a method using the PCR method, there may be used, for example, a method in which primer DNA is prepared by a chemical synthetic method based on base sequences at both ends of DNA to be amplified, and the PCR method is carried out by using the DNA coding the equine interleukin-1 peptide as molding DNA.

A common means of a method of replicating DNA by using the genetic recombination method or the PCR method is described in the literature "Molecular Cloning".

Process for preparing anti-equine interleukin-1 antibody

The anti-equine interleukin-1 antibody according to the present invention can be obtained as, for example, an antiserum and an isolated anti-equine interleukin-1 antibody which are obtained by using the equine interleukin-1 peptide of the present invention as an antigen.

As a process for preparing the antiserum, there may be used, for example, a process in which an animal such as a rabbit and a mouse is immunized by using the equine interleukin-1 peptide of the present invention as an antigen to obtain a serum thereof.

As a process for preparing the anti-equine interleukin-1 antibody by isolation, there may be used, for example, a process in which a rabbit or a mouse is immunized by using the equine interleukin-1 peptide of the present invention as an antigen, spleen cells thereof are fused with myeloma cells to prepare hybridomas, a hybridoma recognizing the equine interleukin-1 peptide described above is selected from the hybridomas, the selected hybridoma is cultured and a culture supernatant thereof is obtained therefrom. In order to heighten antigenicity, if necessary, a suitable carrier protein may be bonded to the equine interleukin-1 peptide of the present invention to be used an immunogen.

As an adjuvant to be used for immunization, there may be used various adjuvants, preferably a Freund's complete adjuvant (FCA) and a Freund's incomplete adjuvant (FIA).

As the myeloma cells, there may be used, for example, P3X63Ag8.653 (ATCC (American Type Culture Collection) CRL-1580) and P3/NSI/1-Ag4-1 (ATCC TIB-18).

As the animal to which the antigen is to be immunized, there may be used, a rabbit, a mouse, a rat, a cow, a sheep, a goat and a chicken, but the kind of animals is not limited to the above examples.

The anti-equine interleukin-1 antibody can be prepared according to a known common means for obtaining an antibody by immunizing art animal except for using the equine interleukin-1 peptide of the present invention as an antigen. As the antibody, there may be mentioned a polyclonal antibody and a Monoclonal antibody.

The antiserum and the anti-equine interleukin-1 antibody prepared by isolation may be modified with various enzymes, colloid or the like.

The obtained antiserum and the anti-equine interleukin-1 antibody prepared by isolation can be used for measuring the concentration of equine interleukin-1 in blood, body fluid, urine or the like, and not only said antiserum and antibody can be used as a reagent for researching relations between equine inflammatory diseases and equine interleukin-1, but also applications of said antiserum and antibody to diagnosis of health conditions and inflammatory diseases of a horse can be expected.

EXAMPLES

The present invention is described in detail by referring to Examples.

Example 1

Preparation of cDNA of equine peripheral blood mononuclear cells (PBMC)

Peripheral blood of a healthy thoroughbred was stratified on Ficoll-Hypaqie (trade name, produced by Lymphoprep Co., Norway), and the resulting material was centrifuged to obtain a peripheral blood mononuclear cell fraction. The peripheral blood mononuclear cell fraction was suspended in a RPMI1640 medium (trade name, produced by Nissui Seiyaku Co., Japan) containing 10% of bovine fetal serum, gentamicin (50 μg/ml) and lipopolysaccharide (5 μg/ml) so as to have a concentration of $1 \times 10^6$ cells/ml. Under existence of 5% (v/v) of carbon dioxide, the suspension was incubated at 37° C. After 24 hours, the suspension was centrifuged to collect cells, and the cells were frozen by liquid nitrogen. By using Fast Track mRNA Isolation Kit (trade name, produced by Invitrogen Co., U.S.A.), Poly(A)+ RNA was extracted from the cells frozen by liquid nitrogen. By using a cDNA-synthesizing kit (produced by Pharmacia Co., Sweden), cDNA was synthesized from Poly(A)+RNA.

Example 2

Acquisition of cDNA of equine interleukin-1α

In order to obtain the entire code area of equine interleukin-1α by using the PCR method, a base sequence (the base sequence represented by SEQ ID NO: 5) located at an upstream side Df the code area of a peptide and a base sequence (the base sequence represented by SEQ ID NO: 6) which was complementary to a base sequence located at a downstream side of said code area among base sequences commonly store(d in human and mouse interleukin-1α genes were used as base sequences of primers to be used for the PCR method.

DNAs having the base sequences of SEQ ID NO: 5 and NO: 6 were chemically synthesized by a DNA-synthesizing machine and used as primers. To the cDNA prepared in EXAMPLE 1 were added each 0.4 mM of these primers, 1.5 unit of Taq polymerase and deoxyribonucleotides to obtain 100 μl of the mixture, and the mixture was amplified by the PCR method. As an amplification operation, a cycle of the respective steps of modification by heating (94° C., 1 minute), annealing by cooling (37° C., 1 minute) and polymerization by incubation (72° C., 1 minute) was repeated 30 times. After the amplification operation, the reaction mixture was subjected to electrophoresis with 2% agarose gel containing ethidium bromide to separate DNAs in the reaction mixture depending on difference in molecular weights (as a molecular weight is smaller, a migration distance is longer), whereby amplified cDNA was obtained. To the obtained cDNA was linked a linker of restriction enzyme EcoRI, and by using TA-Cloning Kit (trade name, produced by Invitrogen Co., U.S.A.), the cDNA to which the linker had been linked was linked to plasmid pCR2 attached to the above kit to obtain a linked mixture. *Escherichia coli* DH5α (trade name, produced by BRL Co., U.S.A.) was used as a host, and a suspension of this *Escherichia coli* and the above linked mixture were mixed. The resulting mixture was sowed on a 2×TY agar plate containing ampicillin (50 mg/ml), 5-bromo-4-chloro-3-indolyl-β-D-galactoside (36 mg/ml) and isopropyl-β-D-thiogalactoside (40 mg/ml) and then cultured. Further, by using Qiagen Plasmid Kit (trade name, produced by Qiagen Co., U.S.A.), *Escherichia coli* containing a recombinant vector into which the cDNA was inserted was selected as a white colony and the colony was obtained. From *Escherichia coli* in the colony, a recombinant plasmid vector into which the cDNA of equine interleukin-1α was Inserted was obtained. The obtained recombinant plasmid vector was named as pCEα.

Example 3
Analysis of base sequence of cDNA of equine interleukin-1α

By using Kilo Sequence Deletion Kit (trade name, produced by Takara Shuzo Co., Japan), exonuclease III and mung bean nuclease, a deletion mutant was prepared from the plasmid obtained in Example 2. By using Auto Read Sequencing Kit (trade name, produced by Pharmacia Co., Sweden), the base sequence of the cDNA of equine interleukin-1α inserted into the plasmid was determined according to the dideoxy termination method. As a result, the obtained cDNA of equine interleukin-1α had the base sequence of SEQ ID NO: 3. As a result of analyzing this base sequence, it was found that the base sequence of SEQ ID NO: 3 coded the amino acid sequence of SEQ ID NO: 1.

EXAMPLE 4
Acquisition of cDNA of equine interleukin-1β

In order to obtain the code area of equine interleukin-1β by using the PCR method, a base sequence (the base sequence represented by, SEQ ID NO: 7) located relatively upstream and a base sequence (the base sequence represented by SEQ ID NO: 8) which was complementary to a base sequence located relatively downstream among base sequences commonly stored in human and mouse interleukin-1β genes were used as base sequences of primers to be used for the PCR method.

DNAs having the base sequences represented by SEQ ID NO: 7 and NO: 8 were chemically synthesized by a DNA-synthesizing machine and used as primers.

According to the procedures described in Example 2 except for using the DNA having the base sequence of SEQ ID NO: 7 and the DNA having the base sequence of SEQ ID NO: 8 as primers, cDNA was amplified. However, it was estimated from judgment of the base sequences of the used primers that the amplified cDNA did not contain the entire code area of equine interleukin-1β. Therefore, procedures for obtaining said entire code area were carried out.

That is, a restriction enzyme EcoRI/NotI adapter was linked to the cDNA obtained in Example 1, and a phage vector lambda ZAP-II (trade name, produced by Stratagene Co., U.S.A.) previously digested with EcoRI was linked thereto. The resulting linked mixture was sealed in a phage shell by using Gigapack Plus (trade name, produced by Stratagene Co., U.S.A.). The sealed mixture was sowed on a NZY plate and then cultured. The obtained plaque was taken out and placed on a nylon membrane filter "Hybond-N" (trade name, produced by Amersham International Co., England).

On the other handle, the above amplified cDNA was labeled with α-$^{32}$P to prepare a probe. The probe was added to a solution containing 50% of formamide, 1% of sodium dodecylsulfate (SDS), 5% of Irish cream, 4×SSPE (here, 1×SSPE is a solution containing 0.18M NaCl, 0.01M sodium phosphate and 1 mM ethylenediaminetetraacetic acid (EDTA)) and 100 mg/ml of modified salmon sperm DNA. The above filter was dipped in the mixture and incubated at 37° C. for 18 hours to effect hybridization. The filter was washed at 37° C. for 3 hours by using an aqueous solution containing 4×SSC (here, 1×SSC is an aqueous solution containing 0.15M NaCl and 0.015M citric acid) and 0.1% of SDS and then subjected to autoradiography at −70° C. A phage giving a positive signal was selected, and to the phage was added a R408 helper phage (trade name, produced by Stratagene Co., U.S.A.) to obtain a recombinant plasmid vector into which an inserting portion of the phage giving a positive signal was inserted into a plasmid vector (pBluescript), i.e., a recombinant plasmid vector containing the cDNA of equine interleukin-1β. The obtained recombinant plasmid vector was named as pEβ5.

Example 5
Analysis of base sequence of cDNA of equine interleukin-1β

Procedures were carried out in the same manner as in Example 3 to determine the base sequence of the cDNA of equine interleukin-1β inserted into the plasmid. As a result, the cDNA of equine interleukin-1β had the base sequence of SEQ ID NO: 4. As a result of analyzing this base sequence, it was found that the base sequence of SEQ ID NO: 4 coded the amino acid sequence of SEQ ID NO: 2.

Example 6
Preparations of transformants by modifying host

The plasmid pCEα obtained in Example 2 and the plasmid pEβ5 obtained in Example 4 were inserted into a *Escherichia coli* JM109 strain, respectively, to prepare transformants by modifying a host. The obtained transformants are deposited as FERM P-15142 (Budapest Treaty deposit FERM BP 6151) and FERM P-15143 (Budapest Treaty deposit FERM BP6152) with National Institute of Bioscience and Human-Technology, Agency of Industrial Science and Technology, Japan, respectively.

The peptide described having SEQ ID NO: 1 or 2 is important for researching relations between equine inflammatory diseases and equine interleukin-1 and useful as a main component of a reagent for such research.

The peptide described having SEQ ID NO: 1 exhibits the effect of the peptide described in the immediately prior paragraph and also is important for researching relations between equine inflammatory diseases and a subtype (α type) of equine interleukin-1 and useful as a main component of a reagent for such research.

The peptide described having SEQ ID NO: 2 exhibits the effect of the peptide described in the foregoing and also is important for researching relations between equine inflammatory diseases and a subtype (β type) of equine interleukin-1 and useful as a main component of a reagent for such research.

The DNA described having SEQ ID NO: 1 or 2 or a DNA sequence complementary thereto is important for researching relations between equine inflammatory diseases and equine interleukin-1 and useful as a main component of a reagent for such research.

The DNA described having SEQ ID NO: 3 or a DNA sequence complementary thereto exhibits the effect of the DNA described above and also is important for researching relations between equine inflammatory diseases and a subtype (α type) of equine interleukin-1 and useful as a main component of a reagent for such research.

The DNA described having SEQ ID NO: 4 or a DNA sequence complementary thereto exhibits the effect of the DNA described above and also is important for researching relations between equine inflammatory diseases and a subtype (β type) of equine interleukin-1 and useful as a main component of e. reagent for such research.

The recombinant vector described having SEQ ID NO: 1 or 2 or a DNA sequence complementary thereto is important for researching relations between equine inflammatory diseases and equine interleukin-1 and can be used for preparing the equine interleukin-1 peptide.

The recombinant vector which plasmid pCEα exhibits the effect of the recombinant vector described having SEQ ID NO: 1 or 2 or a DNA sequence complementary thereto, and also said recombinant is important for researching relations between equine inflammatory diseases and a subtype (α type) of equine interleukin-1 and can be used for preparing the equine interleukin-1α peptide.

The recombinant vector described which is plasmid pEβ5 exhibits the effect of the recombinant vector described having SEQ ID NO: 1 or 2 or a DNA sequence complementary thereto, and also said recombinant is important for researching relations between equine inflammatory diseases and a subtype (β type) of equine interleukin-1 and can be used for preparing the equine interleukin-1β peptide.

The transformant described is important for researching relations between equine inflammatory diseases and equine interleukin-1 and can be used for preparing the equine interleukin-1 peptide.

The transformant deposited as FERM P-15142 exhibits the effect of the transformant described herein, and also said transformant is important for researching relations between equine inflammatory diseases and a subtype (α type) of equine interleukin-1 and can be used for preparing the equine interleukin-1α peptide.

The transformant deposited as FERM P-15143 exhibits the effect of the transformant described herein, and also said transformant is important for researching relations between equine inflammatory diseases and a subtype (β type) of equine interleukin-1 and can be used for preparing the equine interleukin-1β peptide.

The process for preparing an antibody using a peptide having SEQ ID NO: 1 or 2 is suitable for preparing an anti-equine interleukin-1 antibody which is important for researching relations between equine inflammatory diseases and equine interleukin-1 and useful as a main component of a reagent for such research.

We claim:

1. An isolated nucleic acid molecule comprising a nucleotide sequence selected from the group consisting of (a) a nucleotide sequence encoding the amino acid sequence of SEQ ID NO: 1, (b) a nucleotide sequence encoding the amino acid sequence of SEQ ID NO: 2 and (c) a nucleotide sequence which is complementary to (a) or (b).

2. An isolated nucleic acid molecule according to claim 1, produced by a method selected from the group consisting of an isolation method, a chemical synthetic method and a genetic recombination method.

3. An isolated nucleic acid molecule according to claim 1, wherein said isolated nucleic acid is isolated from an equine cell.

4. An isolated nucleic acid molecule according to claim 1, wherein said isolated nucleic acid encodes equine interleukin-1.

5. An isolated nucleic acid molecule comprising a nucleotide sequence selected from the group consisting of (a) a nucleotide sequence of SEQ ID NO:3, (b) a nucleotide sequence of SEQ ID NO:4 and (c) a nucleotide sequence which is complementary to (a) or (b).

6. A recombinant vector which comprises the isolated nucleic acid molecule according to claim 1 or claim 5.

7. A transformant which comprises the vector according to claim 6.

8. The vector according to claim 6, wherein said vector is plasmid pCEα or plasmid pEβ5.

9. A transformant which comprises the vector according to claim 8.

10. An isolated nucleic acid molecule comprising a nucleotide sequence encoding an equine interleukin-1 polypeptide having the amino acid sequence of SEQ ID NO:1 or a nucleotide sequence which is complementary to SEQ ID NO:3.

11. An isolated nucleic acid molecule comprising a nucleotide sequence encoding the amino acid sequence of SEQ ID NO:2, or a nucleotide sequence which is complementary to SEQ ID NO:4.

12. A recombinant vector which comprises the isolated nucleotide sequence according to claim 11.

13. A transformant which comprises the recombinant vector according to claim 12.

14. A transformant comprising a vector comprising a nucleotide sequence encoding an amino acid sequence of SEQ ID NO:1, wherein said vector is plasmid pCEα and wherein said transformant is deposited as FERM BP 6151.

15. A transformant comprising a vector comprising a nucleotide sequence encoding the amino acid sequence of SEQ ID NO:2, wherein said vector is plasmid pEβ5 and wherein said transformant is deposited as FERM BP 6152.

* * * * *

SEQUENCE LISTING

```
(1) GENERAL INFORMATION:

(iii) NUMBER OF SEQUENCES:  8

(2) INFORMATION FOR SEQ ID NO: 1:

(i) SEQUENCE CHARACTERISTICS:
        (A) LENGTH:  270 amino acids
        (B) TYPE: amino acid
        (C) STRANDEDNESS: single strand
        (D) TOPOLOGY: lenear (ii) MOLECULE TYPE: protein (iii) HYPOTHETICAL:

(v) FRAGMENT TYPE:

(vi) ORIGINAL SOURCE:
        (A) ORGANISM:
        (F) TISSUE TYPE:

(x) PUBLICATION INFORMATION:
        (A) AUTHORS: Hirotomo KATO et al.
        (B) TITLE: EQUINE INTERLEUKIN-1 PEPTIDE, DNA CODING
            THE SAME, RECOMBINANT VECTOR CONTAINING THE DNA, TRANS-
            FORMANT CONTAINING THE RECOMBINANT VECTOR AND PROCESS FOR
            PREPARING ANTI-EQUINE INTERLEUKIN-1 ANTIBODY
        (K) RELEVANT RESIDUES IN SEQ ID NO:1: FROM 1 to 270
```

(xi) SEQUENCE DESCRIPTION: SEQ ID NO:1:

Met Ala Lys Val Pro Asp Leu Phe Glu Asp Leu Lys Asn Cys Tyr Ser
                 5                  10                  15

Glu Asn Glu Asp Tyr Ser Ser Glu Ile Asp His Leu Ser Leu Thr Gln
             20                  25                  30

Lys Ser Phe Tyr Asp Ala Ser Tyr Asp Pro Leu Pro Glu Asp Cys Met
             35                  40                  45

Asp Thr Phe Met Ser Leu Ser Thr Ser Glu Thr Ser Lys Thr Ser Lys
     50                  55                  60

Leu Asn Phe Lys Glu Ser Val Val Leu Val Ala Ala Asn Gly Lys Thr
 65                  70                  75                  80

Leu Lys Lys Arg Arg Leu Ser Leu Asn Gln Phe Ile Thr Asn Asp Asp
                 85                  90                  95

Leu Glu Ala Ile Ala Asn Asp Pro Glu Glu Gly Ile Ile Arg Pro Arg
             100                 105                 110

Ser Val His Tyr Asn Phe Gln Ser Asn Thr Lys Tyr Asn Phe Met Arg
             115                 120                 125

Ile Val Asn His Gln Cys Thr Leu Asn Asp Ala Leu Asn Gln Ser Val
 130                 135                 140

Ile Arg Asp Thr Ser Gly Gln Tyr Leu Ala Thr Ala Ala Leu Asn Asn
145                 150                 155                 160

Leu Asp Asp Ala Val Lys Phe Asp Met Gly Ala Tyr Thr Ser Glu Glu
                 165                 170                 175

Asp Ser Gln Leu Pro Val Thr Leu Arg Ile Ser Lys Thr Arg Leu Phe
             180                 185                 190

Val Ser Ala Gln Asn Glu Asp Glu Pro Val Leu Leu Lys Glu Met Pro
             195                 200                 205

Asp Thr Pro Lys Thr Ile Lys Asp Glu Thr Asn Leu Leu Phe Phe Trp
 210                 215                 220

Glu Arg His Gly Ser Lys Asn Tyr Phe Lys Ser Val Ala His Pro Lys
225                 230                 235                 240

Leu Phe Ile Ala Thr Lys Gln Gly Lys Leu Val His Met Ala Arg Gly
                 245                 250                 255

Gln Pro Ser Ile Thr Asp Phe Gln Ile Leu Asp Asn Gln Phe
             260                 265                 270

(2) INFORMATION FOR SEQ ID NO: 2:

(i) SEQUENCE CHARACTERISTICS:
        (A) LENGTH:   268 amino acids
        (B) TYPE: amino acid
        (C) STRANDEDNESS: single strand
        (D) TOPOLOGY: lenear (ii) MOLECULE TYPE: protein (iii) HYPOTHETICAL:

(v) FRAGMENT TYPE:

(vi) ORIGINAL SOURCE:
        (A) ORGANISM:
        (F) TISSUE TYPE:

(x) PUBLICATION INFORMATION:
        (A) AUTHORS: Hirotomo KATO et al.
        (B) TITLE: EQUINE INTERLEUKIN-1 PEPTIDE, DNA CODING
            THE SAME, RECOMBINANT VECTOR CONTAINING THE DNA, TRANS-
            FORMANT CONTAINING THE RECOMBINANT VECTOR AND PROCESS FOR
            PREPARING ANTI-EQUINE INTERLEUKIN-1 ANTIBODY
        (K) RELEVANT RESIDUES IN SEQ ID NO:2: FROM 1 to 268

(xi) SEQUENCE DESCRIPTION: SEQ ID NO:2:

```
Met Ala Ala Val Pro Asp Thr Ser Asp Met Met Thr Tyr Cys Ser Gly
 1               5                  10                  15

Asn Glu Asn Asp Leu Phe Phe Glu Glu Asp Gly Pro Lys Gln Met Lys
                20                  25                  30

Gly Ser Phe Gln Asp Leu Asp Leu Ser Ser Met Gly Asp Gly Gly Ile
            35                  40                  45

Gln Leu Gln Phe Ser His His Leu Tyr Asn Lys Thr Phe Lys His Ala
        50                  55                  60

Met Ser Ile Ile Val Ala Val Glu Lys Leu Lys Lys Ile Pro Val Pro
 65                  70                  75                  80

Cys Ser Gln Ala Phe Gln Asp Asp Leu Arg Ser Leu Phe Ser Val
                85                  90                  95

Ile Phe Glu Glu Glu Pro Ile Ile Cys Asp Asn Trp Asp Glu Gly Tyr
                100                 105                 110

Val Cys Asp Ala Ala Met His Ser Val Asn Cys Arg Leu Arg Asp Ile
            115                 120                 125

Tyr His Lys Ser Leu Val Leu Ser Gly Ala Cys Glu Leu Gln Ala Val
    130                 135                 140

His Leu Asn Gly Glu Asn Thr Asn Gln Gln Val Val Phe Cys Met Ser
145                 150                 155                 160

Phe Val Gln Gly Glu Glu Thr Asp Lys Ile Pro Val Ala Leu Gly
                165                 170                 175

Leu Lys Glu Lys Asn Leu Tyr Leu Ser Cys Gly Met Lys Asp Gly Lys
                180                 185                 190

Pro Thr Leu Gln Leu Glu Thr Val Asp Pro Asn Thr Tyr Pro Lys Arg
            195                 200                 205

Lys Met Glu Lys Arg Phe Val Phe Asn Lys Met Glu Ile Lys Gly Asn
    210                 215                 220

Val Glu Phe Glu Ser Ala Met Tyr Pro Asn Trp Tyr Ile Ser Thr Ser
225                 230                 235                 240

Gln Ala Glu Lys Ser Pro Val Phe Leu Gly Asn Thr Arg Gly Gly Arg
                245                 250                 255

Asp Ile Thr Asp Phe Ile Met Glu Ile Thr Ser Ala
            260                 265         268
```

(2) INFORMATION FOR SEQ ID NO: 3:

(i) SEQUENCE CHARACTERISTICS:
        (A) LENGTH: 810 nucleic acids
        (B) TYPE: nucleic acid
        (C) STRANDEDNESS: double strand
        (D) TOPOLOGY: lenear (ii) MOLECULE TYPE:

(iii) HYPOTHETICAL:

(v) FRAGMENT TYPE: cDNA to mRNA (vi) ORIGINAL SOURCE:
        (A) ORGANISM:
        (F) TISSUE TYPE:

(x) PUBLICATION INFORMATION:
        (A) AUTHORS: Hirotomo KATO et al.
        (B) TITLE: EQUINE INTERLEUKIN-1 PEPTIDE, DNA CODING
           THE SAME, RECOMBINANT VECTOR CONTAINING THE DNA, TRANS-
           FORMANT CONTAINING THE RECOMBINANT VECTOR AND PROCESS FOR
           PREPARING ANTI-EQUINE INTERLEUKIN-1 ANTIBODY
        (K) RELEVANT RESIDUES IN SEQ ID NO:3: FROM 1 to 810

(xi) SEQUENCE DESCRIPTION: SEQ ID NO:3:

```
ATG GCG AAA GTC CCT GAC CTC TTT GAA GAC CTG AAG AAC TGT TAC AGT      48
Met Ala Lys Val Pro Asp Leu Phe Glu Asp Leu Lys Asn Cys Tyr Ser
 1               5                  10                  15

GAA AAT GAA GAC TAC AGT TCT GAA ATT GAC CAT CTC TCT CTG ACT CAG      96
Glu Asn Glu Asp Tyr Ser Ser Glu Ile Asp His Leu Ser Leu Thr Gln
                 20                  25                  30

AAA TCC TTC TAT GAT GCA AGC TAT GAC CCA CTT CCT GAG GAC TGC ATG     144
Lys Ser Phe Tyr Asp Ala Ser Tyr Asp Pro Leu Pro Glu Asp Cys Met
             35                  40                  45

GAT ACA TTT ATG TCT CTG AGC ACC TCT GAA ACC TCT AAG ACA TCC AAG     192
Asp Thr Phe Met Ser Leu Ser Thr Ser Glu Thr Ser Lys Thr Ser Lys
 50                  55                  60

CTG AAC TTC AAG GAG AGC GTG GTG CTG GTG GCA GCC AAC GGG AAG ACT     240
Leu Asn Phe Lys Glu Ser Val Val Leu Val Ala Ala Asn Gly Lys Thr
 65                  70                  75                  80

CTG AAG AAG AGA CGG TTG AGT TTA AAT CAG TTC ATC ACC AAT GAT GAC     288
Leu Lys Lys Arg Arg Leu Ser Leu Asn Gln Phe Ile Thr Asn Asp Asp
                 85                  90                  95

CTG GAA GCC ATT GCC AAT GAT CCA GAA GAA GGA ATC ATC AGG CCC CGA     336
Leu Glu Ala Ile Ala Asn Asp Pro Glu Glu Gly Ile Ile Arg Pro Arg
                100                 105                 110

TCA GTA CAT TAC AAC TTC CAG AGC AAT ACA AAA TAC AAC TTT ATG AGG     384
Ser Val His Tyr Asn Phe Gln Ser Asn Thr Lys Tyr Asn Phe Met Arg
            115                 120                 125

ATC GTC AAC CAC CAG TGT ACT CTG AAT GAT GCC CTC AAT CAA AGT GTA     432
Ile Val Asn His Gln Cys Thr Leu Asn Asp Ala Leu Asn Gln Ser Val
        130                 135                 140

ATT CGA GAC ACA TCA GGT CAA TAT CTT GCG ACT GCT GCA TTA AAT AAT     480
Ile Arg Asp Thr Ser Gly Gln Tyr Leu Ala Thr Ala Ala Leu Asn Asn
145                 150                 155                 160

CTG GAC GAC GCA GTG AAA TTT GAC ATG GGT GCT TAT ACA TCA GAA GAG     528
Leu Asp Asp Ala Val Lys Phe Asp Met Gly Ala Tyr Thr Ser Glu Glu
                165                 170                 175

GAT TCT CAA CTT CCT GTG ACT CTA AGA ATC TCA AAA ACT CGA CTG TTT     576
Asp Ser Gln Leu Pro Val Thr Leu Arg Ile Ser Lys Thr Arg Leu Phe
            180                 185                 190

GTG AGT GCC CAA AAT GAA GAT GAA CCC GTA CTG CTA AAG GAG ATG CCT     624
Val Ser Ala Gln Asn Glu Asp Glu Pro Val Leu Leu Lys Glu Met Pro
        195                 200                 205

GAC ACA CCC AAA ACT ATC AAA GAT GAG ACC AAC CTC CTC TTC TTC TGG     672
Asp Thr Pro Lys Thr Ile Lys Asp Glu Thr Asn Leu Leu Phe Phe Trp
    210                 215                 220

GAA CGT CAC GGC TCT AAG AAC TAC TTC AAA TCG GTT GCC CAT CCA AAG     720
Glu Arg His Gly Ser Lys Asn Tyr Phe Lys Ser Val Ala His Pro Lys
225                 230                 235                 240

TTG TTT ATT GCC ACA AAG CAG GGA AAA CTG GTG CAC ATG GCA AGG GGG     768
Leu Phe Ile Ala Thr Lys Gln Gly Lys Leu Val His Met Ala Arg Gly
                245                 250                 255

CAA CCC TCT ATC ACT GAC TTT CAG ATA TTG GAC AAC CAG TTT             810
Gln Pro Ser Ile Thr Asp Phe Gln Ile Leu Asp Asn Gln Phe
            260                 265                 270
```

(2) INFORMATION FOR SEQ ID NO: 4:

(i) SEQUENCE CHARACTERISTICS:
    (A) LENGTH: 804 nucleic acids
    (B) TYPE: nucleic acid
    (C) STRANDEDNESS: double strand
    (D) TOPOLOGY: lenear (ii) MOLECULE TYPE:

(iii) HYPOTHETICAL:

(v) FRAGMENT TYPE: cDNA to mRNA (vi) ORIGINAL SOURCE:
   (A) ORGANISM:
   (F) TISSUE TYPE:

(x) PUBLICATION INFORMATION:
   (A) AUTHORS: Hirotomo KATO et al.
   (B) TITLE: EQUINE INTERLEUKIN-1 PEPTIDE, DNA CODING
      THE SAME, RECOMBINANT VECTOR CONTAINING THE DNA, TRANS-
      FORMANT CONTAINING THE RECOMBINANT VECTOR AND PROCESS FOR
      PREPARING ANTI-EQUINE INTERLEUKIN-1 ANTIBODY
   (K) RELEVANT RESIDUES IN SEQ ID NO:4: FROM 1 to 804

(xi) SEQUENCE DESCRIPTION: SEQ ID NO:4:

```
ATG GCA GCA GTA CCC GAC ACC AGT GAC ATG ATG ACT TAC TGC AGC GGC      48
Met Ala Ala Val Pro Asp Thr Ser Asp Met Met Thr Tyr Cys Ser Gly
 1               5                  10                  15

AAT GAG AAT GAC CTG TTC TTT GAG GAG GAT GGC CCA AAA CAG ATG AAG      96
Asn Glu Asn Asp Leu Phe Phe Glu Glu Asp Gly Pro Lys Gln Met Lys
                20                  25                  30

GGC AGC TTC CAA GAC CTG GAC CTC AGC TCC ATG GGC GAT GGG GGC ATC     144
Gly Ser Phe Gln Asp Leu Asp Leu Ser Ser Met Gly Asp Gly Gly Ile
        35                  40                  45

CAG CTT CAA TTC TCC CAC CAC CTC TAC AAC AAG ACT TTC AAA CAT GCC     192
Gln Leu Gln Phe Ser His His Leu Tyr Asn Lys Thr Phe Lys His Ala
50                  55                  60

ATG TCA ATC ATT GTG GCT GTG GAG AAG CTG AAG AAG ATA CCC GTT CCC     240
Met Ser Ile Ile Val Ala Val Glu Lys Leu Lys Lys Ile Pro Val Pro
65                  70                  75                  80

TGC TCA CAG GCC TTC CAG GAT GAT GAC TTG AGG AGC CTC TTT TCT GTC     288
Cys Ser Gln Ala Phe Gln Asp Asp Asp Leu Arg Ser Leu Phe Ser Val
                85                  90                  95

ATC TTT GAA GAA GAA CCC ATC ATC TGT GAC AAC TGG GAT GAA GGT TAT     336
Ile Phe Glu Glu Glu Pro Ile Ile Cys Asp Asn Trp Asp Glu Gly Tyr
                100                 105                 110

GTA TGT GAT GCA GCC ATG CAT TCA GTG AAC TGC AGA CTC CGG GAC ATA     384
Val Cys Asp Ala Ala Met His Ser Val Asn Cys Arg Leu Arg Asp Ile
        115                 120                 125

TAC CAT AAA TCC CTG GTG CTG TCC GGT GCA TGT GAG CTG CAG GCT GTC     432
Tyr His Lys Ser Leu Val Leu Ser Gly Ala Cys Glu Leu Gln Ala Val
130                 135                 140

CAC CTC AAT GGA GAG AAT ACA AAC CAA CAA GTG GTG TTC TGC ATG AGC     480
His Leu Asn Gly Glu Asn Thr Asn Gln Gln Val Val Phe Cys Met Ser
145                 150                 155                 160

TTT GTG CAA GGA GAA GAA GAG ACT GAC AAG ATA CCT GTG GCC TTG GGC     528
Phe Val Gln Gly Glu Glu Glu Thr Asp Lys Ile Pro Val Ala Leu Gly
                165                 170                 175

CTC AAG GAA AAG AAC CTG TAC CTG TCT TGT GGG ATG AAA GAT GGG AAG     576
Leu Lys Glu Lys Asn Leu Tyr Leu Ser Cys Gly Met Lys Asp Gly Lys
                180                 185                 190

CCC ACC CTA CAG CTG GAG ACA GTA GAC CCC AAT ACT TAC CCA AAG AGG     624
Pro Thr Leu Gln Leu Glu Thr Val Asp Pro Asn Thr Tyr Pro Lys Arg
        195                 200                 205

AAA ATG GAA AAG CGA TTT GTC TTC AAC AAG ATG GAA ATC AAG GGC AAC     672
Lys Met Glu Lys Arg Phe Val Phe Asn Lys Met Glu Ile Lys Gly Asn
210                 215                 220

GTG GAA TTT GAG TCT GCA ATG TAC CCC AAC TGG TAC ATC AGC ACC TCT     720
Val Glu Phe Glu Ser Ala Met Tyr Pro Asn Trp Tyr Ile Ser Thr Ser
225                 230                 235                 240

CAA GCA GAA AAA AGC CCT GTC TTC CTA GGA AAT ACC AGA GGC GGC CGG     768
```

```
Gln Ala Glu Lys Ser Pro Val Phe Leu Gly Asn Thr Arg Gly Gly Arg
            245                 250                 255
GAC ATA ACT GAC TTC ATC ATG GAA ATC ACC TCT GCC                            804
Asp Ile Thr Asp Phe Ile Met Glu Ile Thr Ser Ala
            260                 265     268
```

(2) INFORMATION FOR SEQ ID NO: 5:

(i) SEQUENCE CHARACTERISTICS:
        (A) LENGTH: 21 nucleic acids
        (B) TYPE: nucleic acid
        (C) STRANDEDNESS: single strand
        (D) TOPOLOGY: lenear (ii) MOLECULE TYPE:

(iii) HYPOTHETICAL:

(v) FRAGMENT TYPE: other nucleic acid, synthesized DNA (vi) ORIGINAL SOURCE:
        (A) ORGANISM:
        (F) TISSUE TYPE:

(x) PUBLICATION INFORMATION:
        (A) AUTHORS: Hirotomo KATO et al.
        (B) TITLE: EQUINE INTERLEUKIN-1 PEPTIDE, DNA CODING
            THE SAME, RECOMBINANT VECTOR CONTAINING THE DNA, TRANS-
            FORMANT CONTAINING THE RECOMBINANT VECTOR AND PROCESS FOR
            PREPARING ANTI-EQUINE INTERLEUKIN-1 ANTIBODY
        (K) RELEVANT RESIDUES IN SEQ ID NO:5: FROM 1 to 21

(xi) SEQUENCE DESCRIPTION: SEQ ID NO:5:

TCATTGGCGT TTGAGTCAGC A                                  21

(2) INFORMATION FOR SEQ ID NO: 6:

(i) SEQUENCE CHARACTERISTICS:
        (A) LENGTH: 22 nucleic acids
        (B) TYPE: nucleic acid
        (C) STRANDEDNESS: single strand
        (D) TOPOLOGY: lenear (ii) MOLECULE TYPE:

(iii) HYPOTHETICAL:

(v) FRAGMENT TYPE: other nucleic acid, synthesized DNA (vi) ORIGINAL SOURCE:
        (A) ORGANISM:
        (F) TISSUE TYPE:

(x) PUBLICATION INFORMATION:
        (A) AUTHORS: Hirotomo KATO et al.
        (B) TITLE: EQUINE INTERLEUKIN-1 PEPTIDE, DNA CODING
            THE SAME, RECOMBINANT VECTOR CONTAINING THE DNA, TRANS-
            FORMANT CONTAINING THE RECOMBINANT VECTOR AND PROCESS FOR
            PREPARING ANTI-EQUINE INTERLEUKIN-1 ANTIBODY
        (K) RELEVANT RESIDUES IN SEQ ID NO:6: FROM 1 to 22

(xi) SEQUENCE DESCRIPTION: SEQ ID NO:6:

GTAAACATTC ATTTAGAATT AC                               22

(2) INFORMATION FOR SEQ ID NO: 7:

(i) SEQUENCE CHARACTERISTICS:
        (A) LENGTH: 24 nucleic acids
        (B) TYPE: nucleic acids
        (C) STRANDEDNESS: single strand
        (D) TOPOLOGY: lenear (ii) MOLECULE TYPE:

-continued

```
    (iii) HYPOTHETICAL:

(v) FRAGMENT TYPE: other nucleic acid, synthesized DNA (vi) ORIGINAL SOURCE:
         (A) ORGANISM:
         (F) TISSUE TYPE:

(x) PUBLICATION INFORMATION:
         (A) AUTHORS: Hirotomo KATO et al.
         (B) TITLE: EQUINE INTERLEUKIN-1 PEPTIDE, DNA CODING
             THE SAME, RECOMBINANT VECTOR CONTAINING THE DNA, TRANS-
             FORMANT CONTAINING THE RECOMBINANT VECTOR AND PROCESS FOR
             PREPARING ANTI-EQUINE INTERLEUKIN-1 ANTIBODY
         (K) RELEVANT RESIDUES IN SEQ ID NO:7: FROM 1 to 24

(xi) SEQUENCE DESCRIPTION: SEQ ID NO:7:

ATGAGGATGA CTTGTTCTTT GAAG                                               24

(2) INFORMATION FOR SEQ ID NO: 8:

(i) SEQUENCE CHARACTERISTICS:
          (A) LENGTH:  22 nucleic acids
          (B) TYPE: nucleic acids
          (C) STRANDEDNESS: single strand
          (D) TOPOLOGY: lenear (ii) MOLECULE TYPE:

(iii) HYPOTHETICAL:

(v) FRAGMENT TYPE: other nucleic acid, synthesized DNA (vi) ORIGINAL SOURCE:
         (A) ORGANISM:
         (F) TISSUE TYPE:

(x) PUBLICATION INFORMATION:
         (A) AUTHORS: Hirotomo KATO et al.
         (B) TITLE: EQUINE INTERLEUKIN-1 PEPTIDE, DNA CODING
             THE SAME, RECOMBINANT VECTOR CONTAINING THE DNA, TRANS-
             FORMANT CONTAINING THE RECOMBINANT VECTOR AND PROCESS FOR
             PREPARING ANTI-EQUINE INTERLEUKIN-1 ANTIBODY
         (K) RELEVANT RESIDUES IN SEQ ID NO:8: FROM 1 to 22

(xi) SEQUENCE DESCRIPTION: SEQ ID NO:8:

GAGGTGCTGA TGTAC CAGTT GG                                                22
```